(12) United States Patent
Horn

(10) Patent No.: US 7,829,745 B1
(45) Date of Patent: Nov. 9, 2010

(54) METHODS FOR SELECTIVELY SYNTHESIZING 1-ARYL-2-TETRALONES

(75) Inventor: Clemens Rudolf Horn, Guibeville (FR)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/542,946

(22) Filed: Aug. 18, 2009

(51) Int. Cl.
*C07C 45/61* (2006.01)
(52) U.S. Cl. .................. 568/312; 568/316; 568/322
(58) Field of Classification Search ............ 568/312, 568/316
See application file for complete search history.

(56) References Cited

U.S. PATENT DOCUMENTS

| | | | |
|---|---|---|---|
| 6,506,538 B1 | 1/2003 | Breyne et al. | |
| 6,969,505 B2 * | 11/2005 | Tonkovich et al. | 423/648.1 |
| 2005/0075325 A1 | 4/2005 | Burnett et al. | |

FOREIGN PATENT DOCUMENTS

| | | |
|---|---|---|
| EP | 0195592 A2 | 9/1986 |
| EP | 1534421 B1 | 9/2006 |

OTHER PUBLICATIONS

Hamann et al. Palladium-Catalyzed Direct alpha-arylation of Ketones. Journal of the American Chemical Society, 19974, vol. 119, p. 12382-12383.*

Kawatsura et al. Simple, Highly Active Palladium Catalysts for Ketone and Malonate Arylation. Joural of the American Chemical Society, 1999,vol. 121, p. 1473-1478.*

Hamann et al. Palladium-Catalyzed Direct Alpha-Arylation of Ketones. Journal of the American Chemical Society, 1997, vol. 119, p. 12382-12383.*

Nathaniel J. Alcock et al.; "Dynamic Kinetic Resolution-Asymmetric Transfer Hydrogenation of 1-Aryl-substituted Cyclic Ketones"; Tetrahedron Asymmetry, vol. 13, Issue 22, 2002, pp. 2485-2490.

Bruce L. Jensen et al., "A Concise Synthesis of 1-Substituted-2-Tetralones by Selective Diol Dehydration Leading to Ketone Transposition"; Tetrahedron Letters, 41, 2000 pp. 6029-6033.

B. Serge Kirkiacharian et al.; "Hydroborations: A New Route for the Preparation of 1-Alkul-(or Aryl) 2-Tetralones"; Synthetic Communication: An International Journal for Rapid Communication of Synthetic Organic Chemistry, 1532-2432, vol. 23, Issue 6, 1993, pp. 737-742.

Joseph M. Fox et al.; "Highly Active and Selective Catalysts for the Formation of α-Aryl Ketones"; J. Am. Chem. Soc., 2000, 122, 1360-1370.

Gabriela A. Grasa et al.; "A Highly Practical and General Route for α-Arylations of Ketones Using BIS-Phosphinoferrocene-Based Palladium Catalysts", Organic Process Research & Development, 2008, 12, 522-529.

* cited by examiner

*Primary Examiner*—Sikarl A Witherspoon
(74) *Attorney, Agent, or Firm*—Robert P. Santandrea

(57) ABSTRACT

Described herein are methods for synthesizing 1-aryl-2-tetralones in an efficient and highly selective manner. The reaction involves a one-step procedure for coupling an aryl halide to a 2-tetralone, where coupling occurs substantially at the 1-position of the 2-tetralone.

16 Claims, 1 Drawing Sheet

METHODS FOR SELECTIVELY SYNTHESIZING 1-ARYL-2-TETRALONES

BACKGROUND

Tetralones are very important intermediates for synthesizing various compounds such as bioactive agents or photochromic dyes. Among the various tetralone compounds, 1-tetralones are relatively inexpensive to make and are readily available. However, 2-tetralones such as 1-aryl-3,4-dihydro-1H-naphthalene-2-one are prepared through complex production processes and are not readily available. The synthesis of 1-substituted-2-tetralones generally requires a multi-step process. For example, the most common method for synthesizing 1-aryl-2-tetralones involves reacting a 1-tetralone B with an aryl magnesium bromide A via a Grignard reaction (Scheme 1). The reaction product C is subsequently dehydrated to produce a double bond (compound D). The double bond is then converted to an epoxide (compound E), which is then converted to the desired 1-aryl-2-tetralone F.

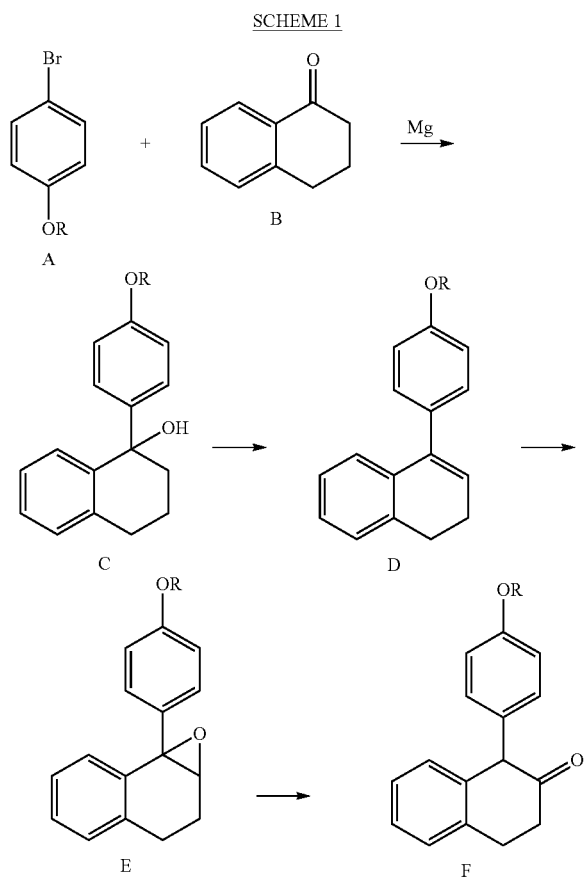

SCHEME 1

In addition to the synthetic procedure depicted in Scheme 1, other methods have been developed to produce 1-aryl-2-tetralones. However, these methods are not selective with respect to the substitution pattern on the 2-tetralone. For example, mixtures of 1-aryl-2-tetralones and 3-aryl-2-tetralones are produced, which requires expensive and tedious separation techniques to isolate the desired 1-aryl-2-tetralone. Therefore, it would be desirable to have synthetic procedure for producing 1-aryl-2-tetralones from 2-tetralone is a highly selective manner and in the least number of reaction steps.

SUMMARY

Described herein are methods for synthesizing 1-aryl-2-tetralones in an efficient and highly selective manner. The reaction involves a one-step procedure for coupling an aryl halide to a 2-tetralone, where coupling occurs substantially at the 1-position of the 2-tetralone. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWING

The accompanying drawing, which is incorporated in and constitutes a part of this specification, illustrates several of the aspects described below.

DETAILED DESCRIPTION

Figure 1:
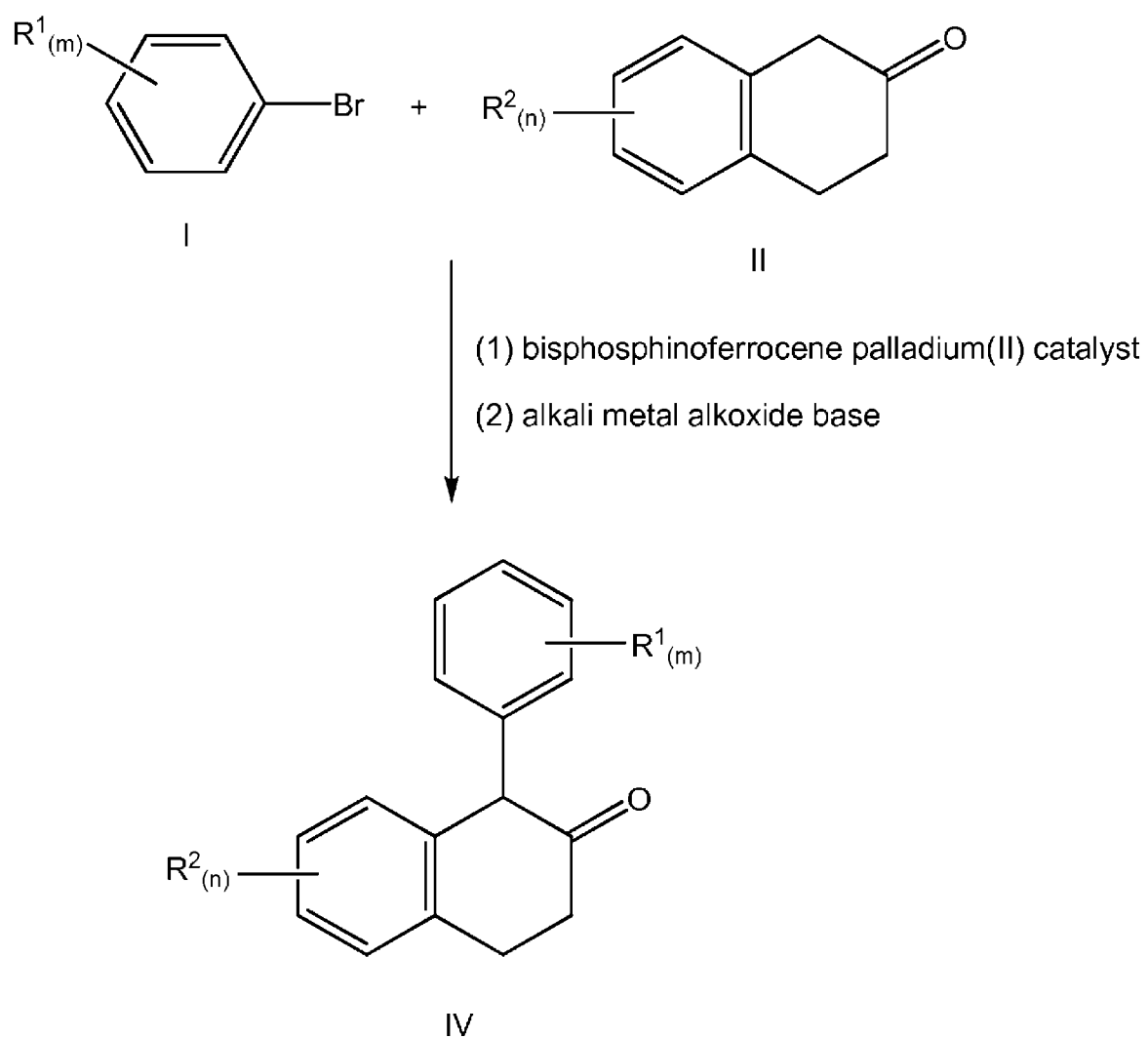
FIG. 1 shows a general reaction scheme for producing 1-aryl-2-tetralones using the methods described herein.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "an alkyl group" can include two or more alkyl groups.

"Optional" or "optionally" means that the subsequently described event or circumstance can or cannot occur, and that the description includes instances where the event or circumstance occurs and instances where it does not.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Variables such as $R^1$-$R^7$, m, n, M, X, and Y used throughout the application are the same variables as previously defined, unless stated to the contrary.

The term "2-tetralone" is also referred to herein as 3,4-dihydro-1H-naphthalene-2-one.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "alkoxy group" is represented by the formula —OR, where R is an alkyl group, an aryl group, or a cycloalkyl group defined herein.

The term "amino group" is represented by the formula —NRR', where R and R' are, independently, hydrogen, and an alkyl group, an aryl group, or a cycloalkyl group defined herein.

The term "carboxylic acid group" is represented by the formula —$CO_2H$. The term "ester group" is represented by the formula —$CO_2R$, where R is an alkyl group, an aryl group, or a cycloalkyl group defined herein. The term "keto group" is represented by the formula —C(O)R, where R is an alkyl group, an aryl group, or a cycloalkyl group defined herein.

The term "perfluoroalkyl group" is an alkyl group as defined herein with at least one hydrogen atom substituted with fluorine.

The term "nitrile group" is represented by the formula —C≡N.

The term "alkenyl group" is defined as substituted or unsubstituted carbon-carbon double bond.

The term "alkynyl group" is defined as substituted or unsubstituted carbon-carbon triple bond.

The term "protected group" is defined as group that is converted from a reactive form to an unreactive form. For example, a keto or aldehyde group can be protected so that it is unreactive. Methods for producing protected groups can be found in, for example, T. W. Greene, P. G. M. Wuts, Protective Groups in Organic Synthesis $3^{rd}$ edition, John Wiley & sons, INC 1999.

Described herein are methods for synthesizing 1-aryl-2-tetralones in a highly efficient and selective manner. In one aspect, the method involves reacting a compound having the formula I

I wherein m is from 1 to 5; and $R^1$ comprises hydrogen, an alkyl group, an alkoxy group, a hydroxy group, an amino group, a carboxylic acid group, an ester, a fluoro group, a perfluoroalkyl group, a nitrile group, an alkenyl, alkynyl group, an aryl group, a protected group, or a fused ring;

with a compound comprising the formula II

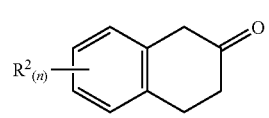

II wherein n is from 1 to 4; and $R^2$ comprises hydrogen, an alkyl group, an alkoxy group, a hydroxy group, an amino group, a carboxylic acid group, an ester, a fluoro group, a perfluoroalkyl group, a nitrile group, an alkenyl, alkynyl group, an aryl group, a protected group, or a fused ring;

in the presence of (1) a bisphosphinoferrocene palladium (II) catalyst and (2) an alkali metal alkoxide base, wherein the 1-aryl-2-tetralone is substantially substituted at the 1-position.

A general reaction scheme for producing 1-aryl-2-tetralones using the methods described herein is provided in FIG. 1. The reaction generally involves coupling the aryl bromide compound I with the 2-tetralone compound II in the presence of (1) a bisphosphinoferrocene palladium (II) catalyst and (2) an alkali metal alkoxide base. A variety of different aryl bromides and 2-tetralones can be used in the methods described herein. For example, the aryl bromide compound I can be substituted with one or more groups, where the groups can be the same or different.

In other aspects, the aryl bromide compound having the formula I can have one or more fused rings bonded to the aryl ring. In one aspect, the aryl bromide has the formula V

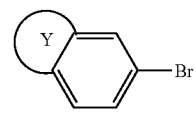

V where Y is a fused aromatic or cycloalkyl group. For example, when m is 2, each $R^1$ can be part of the fused ring. In one aspect, the aromatic group can be composed of a single aromatic ring or two or more fused aromatic rings. The aromatic group can be a heteroaryl group as defined herein as well. In the case when Y is a cycloalkyl group, the fused ring can be a 5-, 6-, 7-, 8-, or 9-membered ring. The cycloalkyl group can be in certain aspects a heteroaryl group as defined herein. For example, the fused ring Y can be a tetrahydrofuran ring. Similar to the aryl bromide having the formula I, the 2-tetralone having the formula II can be unsubstituted ($R^2$ is hydrogen and n is 1) or substituted with a variety of groups.

The coupling of the aryl bromide (formula I) and 2-tetralone (formula II) is performed in the presence of a palladium catalyst and a base. The catalyst useful herein is a bisphosphinoferrocene palladium (II) catalyst. The bisphosphinoferrocene palladium (II) catalyst is generally composed of palladium (II) having at least one bisphosphinoferrocene ligand coordinated to palladium. The bisphosphinoferrocene ligand useful herein is composed of ferrocene [$(Cp)_2Fe$, where Cp=cyclopentadiene] with at least one phosphine group directly or indirectly (e.g., bonded by a linker) to each cyclopentadienyl ring. An example of a bisphosphinoferrocene palladium (II) catalyst useful herein includes

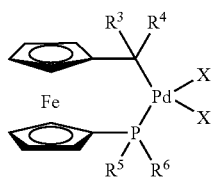

III wherein $R^3$-$R^6$ are, independently, hydrogen, an alkyl group, an aromatic group, or a cycloalkyl group, and wherein $R^3$-$R^6$ are the same or different group, and X comprises an anionic ligand.

In the case of $R^3$-$R^6$, $R^3$-$R^6$ can be the same group or different group. In one aspect, $R^3$-$R^6$ are, independently, a methyl group, ethyl group, n-propyl group, isopropyl group, butyl group, t-butyl group, phenyl group, or a cyclohexyl group. In another aspect, $R^3$-$R^6$ are the same group such as, for example, an alkyl group. In a further aspect, $R^3$-$R^6$ are each a t-butyl group.

With respect to X in formula III, X can be any anionic ligand that can form a bond (e.g., covalent, ionic, electrostatic, etc.) with palladium. For example, X can be a halide (e.g., fluoride, chloride, bromide, iodide), an alkoxide group, a hydroxide, an acetate group, an amino group, or a thiol group. In other aspects, each X in formula III can be linked to one another by a variety of groups. For example, each X can be linked by an ethylene group, where the ligand bonded to palladium in this aspect is ethylene oxide. Thus, each X in formula III can be part of a bidentate ligand. In one aspect, $R^3$-$R^6$ in formula III are each a t-butyl group and each X is chloride.

The alkali metal alkoxide base can be a variety of different compounds including a lithium alkoxide, sodium alkoxide, or potassium alkoxide. The alkali metal alkoxide base is represented by the general formula M-Z, where M is an alkali metal and Z is an alkoxy group as defined herein. In one aspect, the alkali metal alkoxide base has the formula $MOR^7$, wherein M is lithium, sodium, or potassium, and $R^7$ is methyl, ethyl, n-propyl, isopropyl, butyl, t-butyl, or phenyl group. In another aspect, the alkali metal alkoxide base is potassium methoxide.

The procedures for making the 1-ary-2-tetralones described herein involve relatively mild conditions. For example, the palladium (II) catalyst and the alkali metal alkoxide base can be mixed with an organic solvent followed by the addition of the 2-tetralone (formula II) and the aryl bromide (formula I). In general, the molar ratio of 2-tetralone to aryl bromide is about 1:1; however, it is possible to use higher amounts of each compound. In the case of bisphosphinoferrocene palladium (II) catalyst, only a small amount is needed in the reaction. The amount of catalyst used can vary depending upon the desired rate of the reaction. As for the alkali metal alkoxide base, in certain aspects, the molar amount of bases exceeds the molar amount of the 2-tetralone and the aryl bromide. In certain aspects, the reaction can be heated so that the reaction goes to completion. In other aspects, the reaction can be conducted at room temperature. The temperature of the reaction can vary with the selection of the solvents, starting materials, and desired reaction time. Once the reaction is complete, the 1-ary-2-tetralone can be isolated and purified. The Examples section provides exemplary procedures for synthesizing, purifying, and characterizing 1-aryl-2-tetralones using the methods described herein.

The methods described herein can be performed using batch or continuous mode techniques. In one aspect, when the reaction is performed in a continuous mode, microreactors composed of a number of microchannels can be used. For example, the bisphosphinoferrocene palladium (II) catalyst can be applied to the inner surface of a microchannel where a solution of starting materials (e.g., aryl bromide, 2-tetralone, base) are continuously passed through the microchannel and in contact with the catalyst. Methods for producing and using microchannel reactors useful herein can be found in International Publication No. WO 2004/016348, which is incorporated by reference.

The length and width of the microchannel can vary. Similarly, the microchannel can be made of a variety of materials such as, for example, ceramics, iron alloys, glass, and the like. For example, Corning® Advanced-Flow™ reactor, which is a glass microreactor, can be used herein. When it is necessary to control the temperature of the reaction, heat exchangers can be present in the microreactor.

In certain aspects, the bisphosphinoferrocene palladium (II) catalyst can be applied to the inner surface of the microchannels using a variety of techniques. In one aspect, the catalyst can be coated on the inner surface of the microchannel by techniques such as, for example, wash-coating or chemical vapor deposition. In other aspects, the catalyst can be attached to the inner surface of the microchannel by a tether. For example, an organic or inorganic group can be covalently bonded to the inner surface of the microchannel and covalently bonded to the catalyst. In the case of the bisphosphinoferrocene palladium (II) catalyst, the tether can be bonded or attached to the ferrocene group or the phosphine group. In other aspects, the catalyst can be homogeneously dispersed with the starting materials prior to introduction into the microreactor.

The methods described herein produce 1-aryl-2-tetralones substantially substituted at the 1-position. In other words, there is minimal to no substitution at the 3-positions of the 2-tetralone after the reaction is complete (see below).

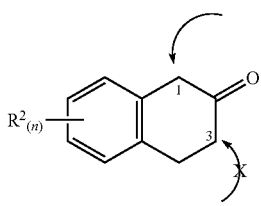

Thus, in one aspect, when the 1-aryl-2-tetralone is substantially substituted at the 1-position, the ratio of 2-tetralone substituted at the 1-position to 2-tetralone substituted at the 3-position is 95 to 5, 98 to 2, or 99 to 1. In another aspect, when the 1-aryl-2-tetralone is substantially substituted at the 1-position, 2-substituted tetralone is completely substituted at the 1-position with no observable substitution at the 3-position. Thus, the methods described herein provide a convenient one-pot synthesis of 1-aryl-2-tetralones in a highly selective manner not observed with current synthetic methodologies.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Synthesis of 1-(4-methoxyphenyl)-3,4-dihydronaphthalen-2(1H)-one

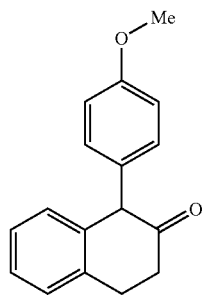

Bis(di-tert-butyl) phosphinoferrocene palladium dichloride (52 mg, 0.08 mmol, 2 mol %) and KOMe (400 mg, 5.7 mmol) were placed in a dry flask under argon atmosphere. THF (5 ml, dry) was added, followed by 2-tetralone (590 mg, 4 mmol dissolved in 5 ml THF (dry)) and 4 bromo anisole (750 mg, 4 mmol dissolved in 5 ml THF (dry)). The resulting mixture was refluxed for 3 h. The THF was removed with reduced pressure. The residue was washed with HCl (1N) and dissolved in dichloromethane. The organic phase was washed with water, dried over $MgSO_4$, filtered and evaporated. The residue was purified by flash column chromatography (hexane/ethyl acetate 90-10→70-30). Only the 1-aryl substituted 2-tetralone was isolated in 95% yield (963 mg, 3.82 mmol). $^1$H NMR (400 MHz, $CDCl_3$) δ 7.36-7.18 (m, 3H), 7.02 (d, J=8.7, 3H), 6.85 (d, J=8.7, 2H), 4.71 (s, 1H), 3.79 (s, 3H), 3.08 (m, 2H), 2.79-2.64 (m, 1H), 2.63-2.57 (m, 1H). $^{13}$C NMR (101 MHz, $CDCl_3$) δ 209.92, 158.78, 136.93, 136.74, 129.74, 129.53, 129.48, 127.91, 127.26, 127.17, 114.13, 59.02, 55.29, 36.92, 28.21.

1-(2,3-dihydrobenzofuran-5-yl)-3,4-dihydronaphthalen-2(1H)-one

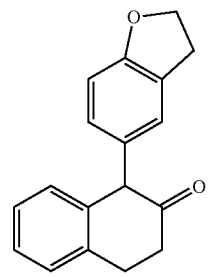

Bis(di-tert-butyl)phosphinoferrocene palladium dichloride (100 mg, 0.15 mmol, 2 mol %) and KOMe (0.63 g, 9 mmol) were placed in a dry flask under argon atmosphere. Dioxane (10 ml, dry) was added followed by the addition of 4-bromo benzodihydrofuran (1.6 g, 8 mmol dissolved in 5 ml dioxane (dry)). The flask was placed into an oil bath (100° C.). 2-Tetralone (1.18 g, 8 mmol dissolved in 10 ml dioxane (dry)) was added dropwise over period of 5 minutes while stirring. The resulting mixture was stirred for 10 minutes. The reaction was stopped when a control performed with TLC showed the complete consumption of 4-bromo benzodihydrofuran. The solution was cooled with an ice bath and HCl (1N, 10 ml) and 100 mL of water were added. Dichloromethane was added to this mixture. The organic phase was separated, and the water phase washed twice with dichloromethane. The combined organic phases were washed with brine, dried over $MgSO_4$, filtered and evaporated. The residue was purified by flash column chromatography (hexane/ethyl acetate, 90-10→70-30). Only the 1-aryl-2-tetralone was isolated in 75% yield (1.59 g, 6.01 mmol), which crystallized while standing. $^1$H NMR (400 MHz, $CDCl_3$) δ 7.33-7.17 (m, 3H), 7.01 (d, J=7.1, 1H), 6.93 (s, 1H), 6.77 (d, J=9.5, 1H), 6.69 (d, J=8.2, 1H), 4.66 (s, 1H), 4.53 (t, J=8.7, 2H), 3.22-2.92 (m, 4H), 2.80-2.47 (m, 2H). $^{13}$C NMR (101 MHz, $CDCl_3$) δ 210.09, 159.35, 136.89, 136.83, 129.54, 129.45, 128.38, 127.86, 127.61, 127.17, 127.11, 125.21, 109.27, 71.36, 59.17, 36.89, 29.68, 28.21. GC-MS (EI): calculated for $C_{18}H_{16}O_2$ 264.32; m/z found 264.2. FT-IR (neat): 1678, 1487, 1280, 1230, 1074.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A method for producing a 1-aryl-2-tetralone, the method comprising reacting a compound comprising the formula I

I wherein m is from 1 to 5; and
  $R^1$ comprises hydrogen, an alkyl group, an alkoxy group, a hydroxy group, an amino group, a carboxylic acid group, an ester, a fluoro group, a perfluoroalkyl group, a nitrile group, an alkenyl, alkynyl group, an aryl group, a protected group, or a fused ring;
with a compound comprising the formula II

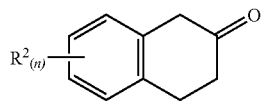

II wherein n is from 1 to 4; and
  $R^2$ comprises hydrogen, an alkyl group, an alkoxy group, a hydroxy group, an amino group, a carboxylic acid group, an ester, a fluoro group, a perfluoroalkyl group, a nitrile group, an alkenyl, alkynyl group, an aryl group, a protected group, or a fused aromatic group or cycloalkyl group;
in the presence of (1) a bisphosphinoferrocene palladium (II) catalyst and (2) an alkali metal alkoxide base,
wherein the 1-aryl-2-tetralone is substantially substituted at the 1-position.

2. The method of claim 1, wherein the compound having the formula I is

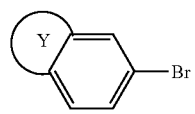

V wherein Y is a fused aromatic or cycloalkyl group.

3. The method of claim 1, wherein the bisphosphinoferrocene palladium(II) catalyst comprises the formula III

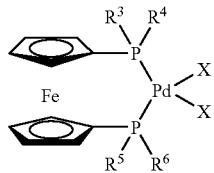

III wherein $R^3$-$R^6$ are, independently, hydrogen, an alkyl group, an aromatic group, or a cycloalkyl group, and wherein $R^3$-$R^6$ are the same or different group, and
X comprises an anionic ligand.

4. The method of claim 3, wherein $R^3$-$R^6$ are the same group.

5. The method of claim 3, wherein $R^3$-$R^6$ are, independently, a methyl group, ethyl group, n-propyl group, isopropyl group, butyl group, t-butyl group, phenyl group, or a cyclohexyl group.

6. The method of claim 3, wherein $R^3$-$R^6$ are the same alkyl group.

7. The method of claim 3, wherein $R^3$-$R^6$ are each a t-butyl group, and each X is a chloride.

8. The method of claim 1, wherein the alkali metal alkoxide base comprises a lithium alkoxide, sodium alkoxide, or potassium alkoxide.

9. The method of claim 1, wherein the alkali metal alkoxide base comprises the formula $MOR^7$, wherein M is lithium, sodium, or potassium, and $R^7$ is methyl, ethyl, n-propyl, isopropyl, butyl, t-butyl, or phenyl group.

10. The method of claim 1, wherein the alkali metal alkoxide base is potassium methoxide.

11. The method of claim 1, wherein the ratio of 2-tetralone substituted at the 1-position to 2-tetralone substituted at the 3-position is 95 to 5.

12. The method of claim 1, wherein the ratio of 2-tetralone substituted at the 1-position to 2-tetralone substituted at the 3-position is 98 to 2.

13. The method of claim 1, wherein the ratio of 2-tetralone substituted at the 1-position to 2-tetralone substituted at the 3-position is 99 to 1.

14. The method of claim 1, wherein the 2-substituted tetralone is completely substituted at the 1-position.

15. The method of claim 1, wherein the method is performed in continuous mode.

16. The method of claim 15, wherein the method is performed in a microreactor.

* * * * *